(12) United States Patent
Kwok et al.

(10) Patent No.: US 10,334,687 B2
(45) Date of Patent: Jun. 25, 2019

(54) MULTISPECTRAL SWITCH FIBER OPTIC LIGHTING LARYNGOSCOPE

(71) Applicant: Ngok Wing Jimmy Kwok, Tai Po, N.T. (HK)

(72) Inventors: Ngok Wing Jimmy Kwok, Tai Po (HK); Kevin Lam Hiu Young, Tai Po (HK)

( * ) Notice: Subject to any disclaimer, the term of this patent is extended or adjusted under 35 U.S.C. 154(b) by 51 days.

(21) Appl. No.: 15/493,067

(22) Filed: Apr. 20, 2017

(65) Prior Publication Data
US 2018/0310378 A1   Oct. 25, 2018

(51) Int. Cl.
| | |
|---|---|
| *A61B 1/267* | (2006.01) |
| *H05B 33/08* | (2006.01) |
| *F21S 9/02* | (2006.01) |
| *F21V 8/00* | (2006.01) |
| *F21V 19/00* | (2006.01) |
| *F21V 29/89* | (2015.01) |
| *A61B 1/06* | (2006.01) |
| *A61B 1/07* | (2006.01) |
| *F21Y 115/10* | (2016.01) |

(52) U.S. Cl.
CPC ....... *H05B 33/0857* (2013.01); *A61B 1/0638* (2013.01); *A61B 1/07* (2013.01); *A61B 1/267* (2013.01); *F21S 9/02* (2013.01); *F21V 19/003* (2013.01); *F21V 29/89* (2015.01); *G02B 6/0005* (2013.01); *G02B 6/0096* (2013.01); *H05B 33/0845* (2013.01); *F21Y 2115/10* (2016.08)

(58) Field of Classification Search
CPC ............ A61B 1/267–2676; A61B 1/06; A61B 1/0638
See application file for complete search history.

(56) References Cited

U.S. PATENT DOCUMENTS

| | | | | |
|---|---|---|---|---|
| 4,729,367 A | * | 3/1988 | Bauman ................. | A61B 1/267 600/198 |
| 4,938,205 A | * | 7/1990 | Nudelman ........... | A61B 1/0008 257/E31.115 |
| 5,172,685 A | * | 12/1992 | Nudelman ......... | A61B 1/00193 257/E31.115 |

(Continued)

*Primary Examiner* — Eduardo C Robert
*Assistant Examiner* — Michelle C Eckman
(74) *Attorney, Agent, or Firm* — Intellectual Property Law Group LLP

(57) ABSTRACT

A multispectral switch fiber optic lighting laryngoscope comprising: a laryngoscope handle configured with a connection part, and the connection part mechanically connects and fastens a laryngoscope blade. Configured in the laryngoscope handle is a LED light module that comprises a multispectral LED light which emits at least two different colors of light. Configured in the laryngoscope handle is a PCB module that comprises a control circuit and a switch button. The control circuit is electrically connected with the switch button and the multispectral LED light respectively, enabling a user to switch the color of emitted light and adjust radiation brightness from the multispectral LED light through pressing the switch button. The fiber optic lighting laryngoscope enables physicians to conveniently switch different colors of light for illumination in accordance with different and complex operation environments, thus helping physicians to better identify laryngeal, trachea, and obstructing objects and ensuring smooth progress of laryngeal surgery or other treatments.

9 Claims, 3 Drawing Sheets

(56) References Cited

U.S. PATENT DOCUMENTS

| | | | | |
|---|---|---|---|---|
| 5,575,758 A * | 11/1996 | Easterbrook, III | A61B 1/267 | 600/190 |
| 5,800,344 A * | 9/1998 | Wood, Sr. | A61B 1/267 | 600/185 |
| 5,879,289 A * | 3/1999 | Yarush | A61B 1/00039 | 600/109 |
| D630,737 S * | 1/2011 | Tenger | | D24/137 |
| D630,738 S * | 1/2011 | Tenger | | D24/137 |
| 8,029,440 B2 * | 10/2011 | Birnkrant | A61B 1/00105 | 600/112 |
| 8,394,016 B1 * | 3/2013 | Arne' | A61B 1/267 | 600/193 |
| 9,179,831 B2 * | 11/2015 | McGrail | A61B 1/00016 | |
| 9,386,914 B2 * | 7/2016 | Birnkrant | A61B 1/00105 | |
| 2002/0087050 A1 * | 7/2002 | Rudischhauser | A61B 1/267 | 600/199 |
| 2004/0210114 A1 * | 10/2004 | Simon | A61B 1/00032 | 600/185 |
| 2005/0251119 A1 * | 11/2005 | Eaton | G02B 6/0008 | 606/15 |
| 2007/0093693 A1 * | 4/2007 | Geist | A61B 1/267 | 600/199 |
| 2007/0112257 A1 * | 5/2007 | Hensler | A61B 1/0676 | 600/199 |
| 2007/0230167 A1 * | 10/2007 | McMahon | A61B 1/303 | 362/157 |
| 2008/0082045 A1 * | 4/2008 | Goldfarb | A61B 1/00126 | 604/96.01 |
| 2008/0228038 A1 * | 9/2008 | McMahon | A61B 1/00105 | 600/223 |
| 2008/0234549 A1 * | 9/2008 | Geist | A61B 1/07 | 600/194 |
| 2009/0076334 A1 * | 3/2009 | Chen | A61B 1/303 | 600/223 |
| 2009/0198108 A1 * | 8/2009 | Chen | A61B 1/00103 | 600/220 |
| 2009/0209816 A1 * | 8/2009 | Gunther Nielsen | A61B 1/267 | 600/118 |
| 2009/0318767 A1 * | 12/2009 | Tenger | A61B 1/0676 | 600/194 |
| 2009/0318768 A1 * | 12/2009 | Tenger | A61B 1/0676 | 600/194 |
| 2009/0318769 A1 * | 12/2009 | Tenger | A61B 1/043 | 600/199 |
| 2010/0022843 A1 * | 1/2010 | Pecherer | A61B 1/00034 | 600/197 |
| 2010/0036260 A1 * | 2/2010 | Zuluaga | A61B 1/00142 | 600/476 |
| 2010/0152541 A1 * | 6/2010 | Tenger | A61B 1/0676 | 600/194 |
| 2010/0191067 A1 * | 7/2010 | Chen | A61B 1/00052 | 600/245 |
| 2011/0028790 A1 * | 2/2011 | Farr | A61B 1/00052 | 600/187 |
| 2011/0282160 A1 * | 11/2011 | Bhadri | A61B 3/0008 | 600/236 |
| 2012/0035502 A1 * | 2/2012 | Menegazzi | A61B 1/0008 | 600/567 |
| 2012/0229615 A1 * | 9/2012 | Kirma | A61B 1/00181 | 348/68 |
| 2012/0330103 A1 * | 12/2012 | Tenger | A61B 1/043 | 600/188 |
| 2012/0330104 A1 * | 12/2012 | Tenger | A61B 1/0684 | 600/191 |
| 2013/0128223 A1 * | 5/2013 | Wood | A61B 5/0077 | 351/206 |
| 2014/0005484 A1 * | 1/2014 | Charles | A61B 17/02 | 600/201 |
| 2014/0160261 A1 * | 6/2014 | Miller | A61B 1/00052 | 348/77 |
| 2014/0272764 A1 * | 9/2014 | Miller | A61B 1/0684 | 433/27 |
| 2015/0141866 A1 * | 5/2015 | Mayse | A61B 10/04 | 600/564 |
| 2015/0150439 A1 * | 6/2015 | Ruiz | A61B 1/267 | 600/186 |
| 2015/0238070 A1 * | 8/2015 | Lia | A61B 1/0676 | 600/223 |
| 2015/0354758 A1 * | 12/2015 | St. George | G02B 6/0008 | 362/553 |
| 2016/0038012 A1 * | 2/2016 | McMahon | A61B 1/06 | 600/210 |
| 2016/0058276 A1 * | 3/2016 | Ramos Da Silva | A61B 1/00034 | 600/196 |
| 2016/0061390 A1 * | 3/2016 | Osten | A61B 1/0638 | 362/231 |
| 2016/0213236 A1 * | 7/2016 | Hruska | A61B 1/267 | |
| 2016/0256047 A1 * | 9/2016 | Newcomb | A61B 1/267 | |
| 2017/0071509 A1 * | 3/2017 | Pandey | A61B 5/12 | |
| 2017/0135566 A1 * | 5/2017 | Gerrans | A61B 1/012 | |
| 2018/0008138 A1 * | 1/2018 | Thommen | A61B 1/3132 | |
| 2018/0098692 A1 * | 4/2018 | Cantrell | A61B 1/267 | |
| 2018/0146839 A1 * | 5/2018 | Friedlander | A61B 1/015 | |
| 2018/0214009 A1 * | 8/2018 | Endo | A61B 1/00186 | |

* cited by examiner

MULTISPECTRAL SWITCH FIBER OPTIC LIGHTING LARYNGOSCOPE

BACKGROUND OF INVENTION

1. Field of Invention

The present application relates to the medical devices area, and particularly relates to a multispectral switch fiber optic lighting laryngoscope.

2. Background

Laryngoscope is a critical medical device for patients' airway management, and laryngoscope is used for various tracheal intubation detection and surgery, including airway laryngoscopy. The application environments of Laryngoscope are complex, and different body conditions and inner structures of patients impose very high requirements on laryngoscope in use to deal with high larynx position, premaxillodental protrusion, tongue root shift, glossauxesis, cervical spine injury, small mouth openness, degenerating jaw bones and so on; moreover, when using laryngoscope, physicians often need to cope with bleeding, obstruction from vomiting, and changing degenerating human body condition. Current laryngoscope can only provide white light, making it difficult to effectively illuminate all the above complex environments, and physicians cannot identify inner structures and obstructing objects in the larynx well as a result.

SUMMARY OF INVENTION

To overcome the deficiency of current laryngoscope providing only white color for illumination, the objective of the present invention is to provide a multispectral switch fiber optic lighting laryngoscope that enables physicians to freely switch different colors of light as well as different radiation brightness for various complex surgery and detention environments.

The present application is realized in this way: a multispectral switch fiber optic lighting laryngoscope, comprises a laryngoscope handle, said laryngoscope handle is configured with a connection part, said connection part mechanically connects and fastens a laryngoscope blade.

Advantageously, wherein an LED light module is configured in said laryngoscope handle, and said LED light module comprises a multispectral LED light, said multispectral LED light emits at least two different colors of light;

Advantageously, wherein a PCB module is configured in said laryngoscope handle, and said PCB module comprises a control circuit and a switch button;

Advantageously, wherein said control circuit is electrically connected with said switch button and said multispectral LED light respectively, enabling a user to switch the color of emitted light and adjust radiation brightness from said multispectral LED light through pressing said switch button.

Advantageously, said LED light module further comprises an auxiliary PCB board, said multispectral LED light is set up on and electrically connected with said auxiliary PCB board; and said LED light module further comprises a light guiding tube, said light guiding tube is configured surrounding said multispectral LED light.

Advantageously, said PCB module further comprises a main PCB board and a battery, said switch button is set up on and electrically connected with said main PCB board; said battery is electrically connected with said main PCB board;

Advantageously, said main PCB board and said auxiliary PCB board is electrically connected.

Advantageously, a fiber optic tube is configured in said laryngoscope blade, and an optical fiber is configured in said fiber optic tube.

Advantageously, when said connection part mechanically connects and fastens a laryngoscope blade, said fiber optic tube and light guiding tube are physically and optically connected, enabling the light emitted from said multispectral LED light pass though said light guiding tube and the optical fiber in said fiber optic tube towards a light emitting tip (210) of said laryngoscope blade.

Advantageously, said light guiding tube comprises a wide light guiding section and a narrow light guiding section, a semicircular tube is configured between said wide light guiding section and narrow light guiding section for smooth transition of light, maximizing the accumulation and transfer of light emitted from said multispectral LED light; and wherein said light guiding tube is made of polycarbonate or polymethyl methacrylate materials.

Advantageously, said auxiliary PCB board and main PCB board are made of metal substrate materials; said connection part is a general connection hinge.

Advantageously, said control circuit comprises a boosted circuit and a main control chip, said boosted circuit is electrically connected with said battery and main control chip respectively; said switch button is electrically connected with said main control chip.

Advantageously, said control circuit further comprises a first radiation brightness adjustment circuit and a second radiation brightness adjustment circuit, and said first radiation brightness adjustment circuit is electrically connected with said main control chip through a first circuit and a second circuit respectively, said first radiation brightness adjustment circuit is electrically connected with said multispectral LED light.

Advantageously, said second radiation brightness adjustment circuit is electrically connected with said main control chip through a third circuit and a fourth circuit respectively, said second radiation brightness adjustment circuit is electrically connected with said multispectral LED light.

The beneficial effect of the present application is that the multispectral switch fiber optic lighting laryngoscope enables physicians to freely switch different colors of light as well as different radiation brightness for various complex surgery and detention environments, such that physicians can more effectively observe inner environments and obstructing objects within the larynx, and more smoothly undertakes

DETAILED DESCRIPTION OF EMBODIMENTS OF THE INVENTION

The multispectral switch fiber optic lighting laryngoscope of the present application will now be described in further detail with reference to the accompanying drawings.

Figure 1:
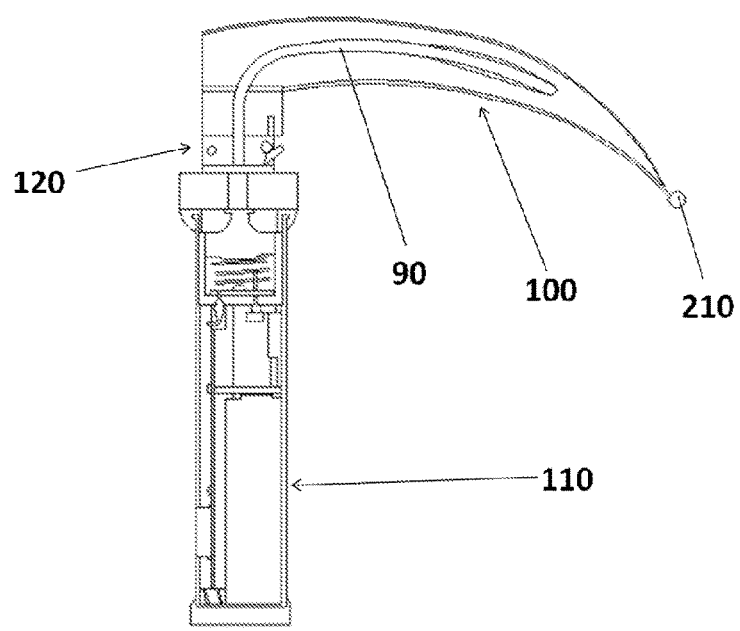
FIG. 1 shows the overall structure of the multispectral switch fiber optic lighting laryngoscope in the art.

FIG. 1 shows the overall structure of the multispectral switch fiber optic lighting laryngoscope in the art. The multispectral switch fiber optic lighting laryngoscope comprises a laryngoscope handle 110, and the laryngoscope handle 110 is configured with a connection part 120, and the connection part 120 mechanically connects and fastens a laryngoscope blade 100. The connection part 120 can be a general connection hinge.

Figure 2:
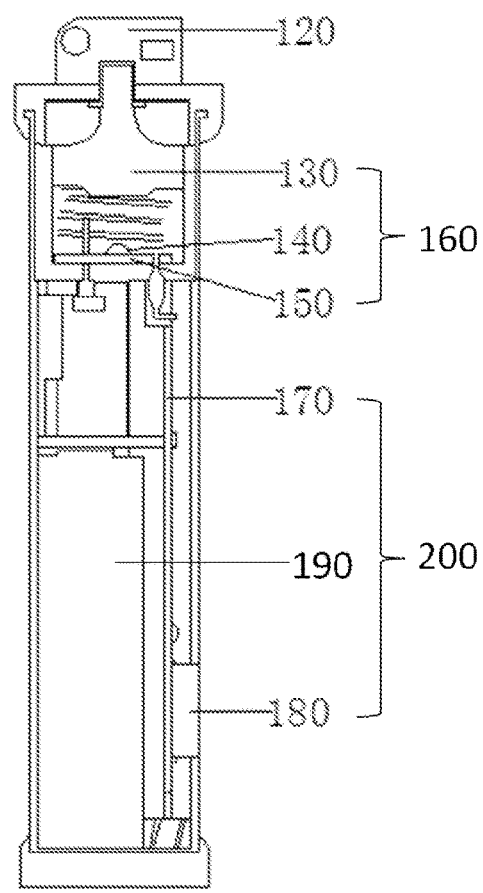
FIG. 2 shows the inside structure of the laryngoscope holder of the multispectral switch fiber optic lighting laryngoscope according to the present application.

FIG. 2 shows the inside structure of the laryngoscope holder of the multispectral switch fiber optic lighting laryngoscope according to the present application. An LED light module 160 is configured in the laryngoscope handle 110, and the LED light module 160 comprises an auxiliary PCB board 150, a multispectral LED light 140 that is electrically connected with the auxiliary PCB board 150, and a light guiding tube 130. The light guiding tube 130 is configured surrounding the multispectral LED light 140. The multispectral LED light 140 is able to emit at least two different colors of light. When facing a wide variety of complex environments inside the larynx, physicians need different colors of light for illumination in order to better identify and judge the conditions and any blocking objects within the larynx, thus ensuring good progress of laryngeal surgery or other treatments.

When undertaking intubation operations, due to the unstable condition of patients' bodies, physicians often would deal with sudden change of Laryngeal structure, internal bleeding, or blockage of sight by foreign objects; and the color of the internal structure of larynx, along with various colors of possible internal bleeding, blocking objects, products of digestion, and vomit, as well as the colors of these combined substance, makes physicians very difficult to identify and judge the medical condition in the larynx by using a single-color lighting laryngoscope in a laryngeal surgery. Whereas the multispectral LED light 140 in the present invention can emit at least two different colors of light along with different degrees of radiation brightness, which provides must better medical assistance to physicians.

For the interaction between an object and light, when using warm color light to illuminate warn color objects, there is very high effective reflection luminance, and the illuminated object has higher light saturation; similarly, when using cold color light to illuminate cold color objects, the effective reflection luminance is higher than using light of other colors. Using a light source that matches the reflectivity of an object, there results a higher luminivity reflectivity for such object with better luminous effect. Advantageously, the multispectral LED light 140 can be a three chip RGB LED light or a four chip WRGB LED light.

Luminance is used to describe the luminous intensity of a surface in a given direction per unit of projected area of an object, and the reflection luminance by human's eye perception is regarded effective luminance, and a related key parameter is reflectivity. In the conventional application of illumination, average reflectivity is used to indicate the reflectivity of an object; the average reflectivity for objects with relatively low light saturation remains fairly stable, but the average reflectivity varies substantially for objects with relatively high light saturation. To increase the effective reflection luminance, it largely depends upon the color of emitted light and emission efficiency of light source; conventional laryngoscope using white color light illumination is a mature product, and the emission efficiency of light source cannot be higher; in contrast, the emission efficiency of the multispectral LED light 140 can be improved by the control circuit. Additionally, it is important to take note that the multispectral LED light 140 has a variety of spectral selection, which can be individually selected and controlled to achieve the optimal effective reflection luminance. Therefore, different colors of emitted light by the multispectral LED light 140 can be applied towards objects with different reflectivity, achieving better effective reflection luminance. This provides great assistance for physicians to accurately identify the inner structure of larynx, and satisfies the requirement for different colors of emitted light for optimal effective reflection luminance purpose in the laryngeal surgery.

Additionally, the laryngoscope in this invention uses the multispectral LED light 140 with a single light bulb as the light source, substantially enhancing the stability of the light source.

The multispectral LED light 140 is set up and fixed on the auxiliary PCB board 150, and the auxiliary PCB board 150 and the main PCB board 170 are both made of metal substrate materials with good heat conduction and heat dissipation. The metal substrate materials can be copper foil substrate or metal base copper clad laminate with aluminum or iron. The heat generated by the multispectral LED light 140 can be quickly dissipated by the multispectral LED light 140. Two ends of the auxiliary PCB board 150 are in contact with the inner walls of the laryngoscope handle 110, assisting the auxiliary PCB board 150 to transfer the heat from the multispectral LED light 140 to the laryngoscope handle 110, which makes sure the multispectral LED light 140 always remains in a low temperature working environment and keeps a stable light emission condition.

A PCB module 200 is configured in the laryngoscope handle 110, and the PCB module includes a main PCB board 170, a switch button 180 that is set up on the main PCB board 170, and a battery 190 that is electrically connected with the main PCB board 170. The switch button 180 is electrically connected with the main PCB board 170. The PCB module 200 further includes a control circuit (not shown), and the control circuit is electrically connected with the switch button 180 and the multispectral LED light 140 respectively. Users can change the color of the emitted light from the multispectral LED light 140 by pressing the switch button 180. The main PCB board 170 is also electrically connected with the auxiliary PCB board 150.

The main PCB board 170 is configured vertically to the bottom face of the laryngoscope handle 110, and the main PCB board 170 is configured parallel to the side wall of the laryngoscope handle 110. The switch button 180 is set up on the side wall of the laryngoscope handle 110, making it convenient for physicians to press the button by using the fingers to switch the colors of emitted light from the multispectral LED light 140. The base of the switch button 180 is set up on the main PCB board 170, and the switch button 180 is electrically connected with the control circuit on the main PCB board 170. The battery 190 is electrically connected with the multispectral LED light 140 via the main PCB board 170 and the auxiliary PCB board 150, and provides electricity to the multispectral LED light 140. The main PCB board 170 is also made of materials with good heat conduction and heat dissipation, and the top end of the main PCB board 170 is in contact with the auxiliary PCB board 150, further assisting the auxiliary PCB board 150 to transfer heat from the multispectral LED light 140.

A fiber optic tube 90 is configured in the laryngoscope blade 100, and an optical fiber is configured in the fiber optic tube 90. The connection part 120 mechanically connects and fastens a laryngoscope blade 100, and the fiber optic tube 90 and light guiding tube 130 are physically and optically connected, enabling the light emitted from the multispectral LED light 140 pass through the light guiding tube 130 and the optical fiber in the fiber optic tube 90 towards a light emitting tip 210 of the laryngoscope blade 100.

The multispectral LED light 140 is configured in the laryngoscope handle 110 instead of the laryngoscope blade 100, and such configuration is able to conveniently set apart the removable laryngoscope blade 100 and the laryngoscope handle 110, and separately undergoes high temperature and pressure bacteria disinfection towards the laryngoscope blade 100, thus saving the laryngoscope handle 110 from additional disinfection procedure and avoiding potential damage by the procedure.

Figure 3:
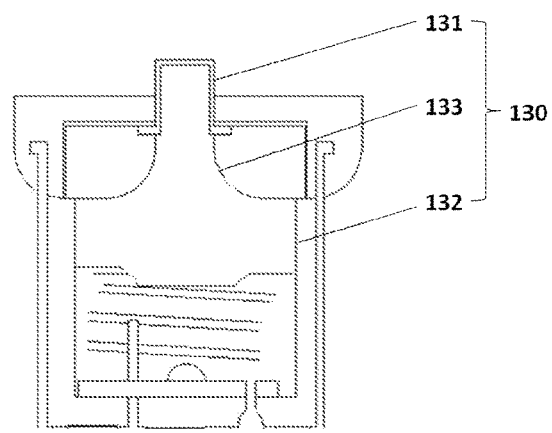
FIG. 3 shows the structure of the light guiding tube of the multispectral switch fiber optic lighting laryngoscope according to the present application.

FIG. 3 shows the structure of the light guiding tube of the multispectral switch fiber optic lighting laryngoscope according to the present application. The light guiding tube 130 comprises a wide light guiding section 131 and a narrow light guiding section 132, and a semicircular tube 133 is configured between the wide light guiding section 131 and the narrow light guiding section 132 for the purpose of smooth transition of light. The tube of the light guiding tube 130 has the wide light guiding section 131 surrounding the light source, and the tube narrows gradually and smoothly towards the narrow light guiding section 132 via the semicircular tube 133, maximizing the accumulation and transfer of light emitted from the multispectral LED light 140 to the optical fiber in the fiber optic tube 90.

The light guiding tube 130 is made of polycarbonate or polymethl methacrylate materials.

Figure 4:
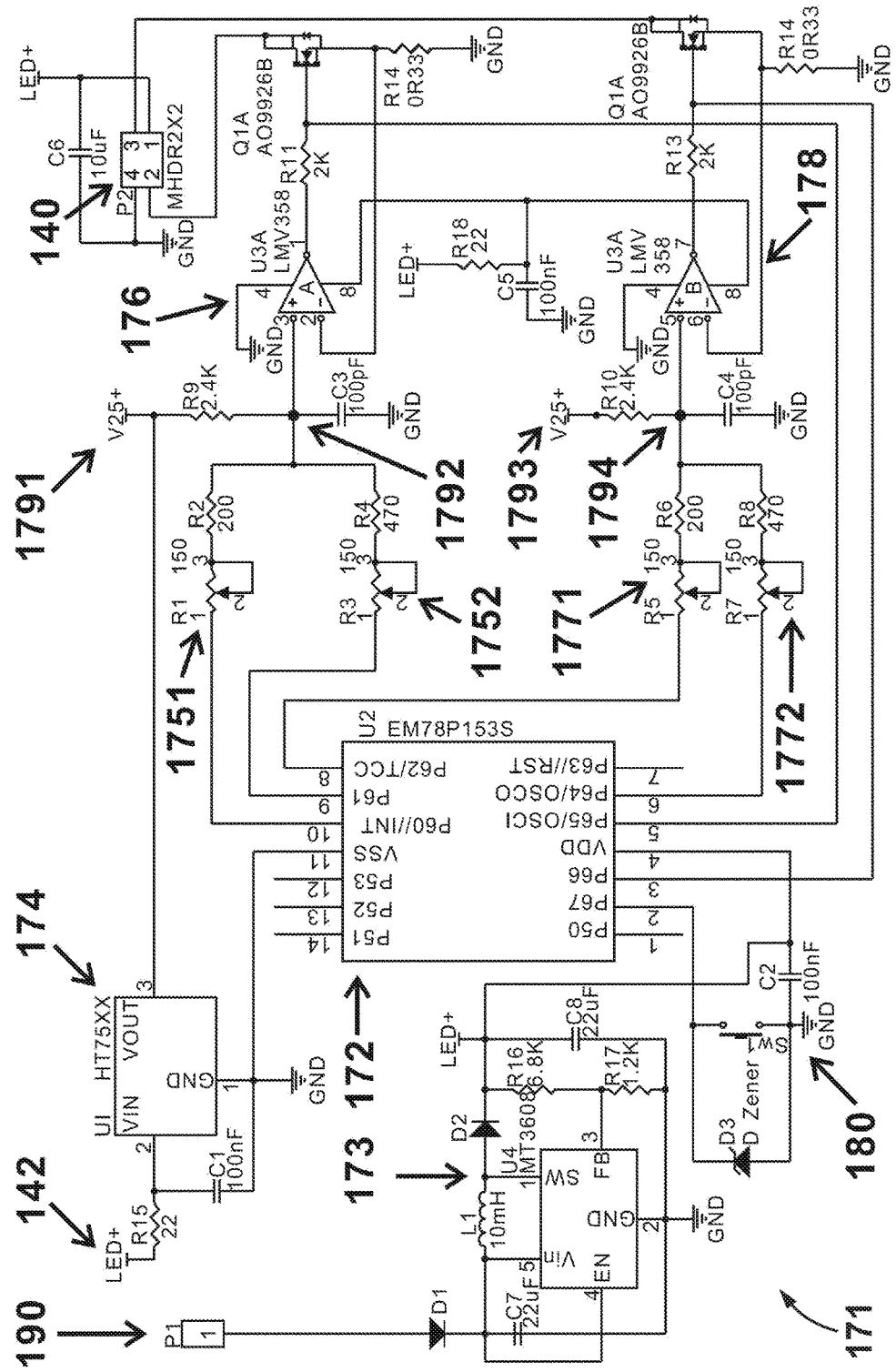
FIG. 4 shows the control circuit of the multispectral switch fiber optic lighting laryngoscope according to the present application.

FIG. 4 shows the control circuit of the multispectral switch fiber optic lighting laryngoscope according to the present application. The control circuit 171 comprises a boosted circuit 173 and a main control chip 172, and the boosted circuit 173 is electrically connected with the battery 190 and the main control chip 172 respectively. The switch button 180 is electrically connected with the main control chip 172.

The control circuit 171 includes a first radiation brightness adjustment circuit 176 and a second radiation brightness adjustment circuit 178. The first radiation brightness adjustment circuit 176 is electrically connected with the main control chip 172 through a first circuit 1751 and a second circuit 1752 respectively, and the first radiation brightness adjustment circuit 176 is electrically connected with the multispectral LED light 140.

the second radiation brightness adjustment circuit 178 is electrically connected with the main control chip 172 through a third circuit 1771 and a fourth circuit 1772 respectively, and the second radiation brightness adjustment circuit 178 is electrically connected with the multispectral LED light 140.

The voltage provided by the battery 190 is boosted via the boosted circuit 173, and forms boosted input voltage 142; the VSS port of the main control chip 172 is electrically connected with the boosted input voltage 142. The VIN port of the voltage stabilization integrated chip 174 is electrically connected with the boosted input voltage 142, and the VOUT port of the voltage stabilization integrated chip 174 outputs stable voltage, and forms a first voltage input port 1791 (shown as V25+ in FIG. 4); the first voltage input port 1791 is electrically connected with a first node 1792 through the resistance R9; the first node 1792 is electrically connected with the first circuit 1751 and a second circuit 1752; the first node 1792 is also electrically connected with the first radiation brightness adjustment circuit 176, in order to realize that the first voltage input port 1791 provides different voltage to adjust and control one color of the emitted light as well as the light brightness from the multispectral LED light 140.

Similarly, the stable voltage outputted by the VOUT port of the voltage stabilization integrated chip 174 also forms a second voltage input port 1793 (also shown as V25+ in FIG. 4), and the second voltage input port 1793 is electrically connected with a second node 1794 via resistance R10; the second node 1794 is also electrically connected with a third circuit 1771 and a fourth circuit 1772; the second node is also electrically connected with the second radiation brightness adjustment circuit 178, in order to realize that the second voltage input port 1793 provides different voltage to adjust and control another color of the emitted light as well as the light brightness from the multispectral LED light 140.

The P60//INT port of the main control chip 172 is electrically connected with the first circuit 1751, and the P61 port of the main control chip 172 is electrically connected with the second circuit 1752, and the main control chip 172 controls and adjusts the voltage of the first voltage input port 1791 through the first circuit 1751 and a second circuit 1752.

Similarly, the P62/TCC port of the main control chip 172 is electrically connected with the third circuit 1771, and the P64/OSCO port of the main control chip 172 is electrically connected with the fourth circuit 1772, and the main control chip 172 controls and adjusts the voltage of the second voltage input port 1793 through the third circuit 1771 and the fourth circuit 1772.

Additionally, two ends of the switch button 180 are electrically connected with the P67 port and VDD port of the main control chip 172, thus realizing the beneficial and advantageous effect of pressing switch button 180 to change the colors of emitted light as well as the light brightness from the multispectral LED light 140. Such beneficial and advantageous effect would enable physicians to conveniently change the colors of light as well as the radiation brightness for illumination purpose in accordance with different complex situations, and better assists physicians to identify the larynx, trachea, and other blocking objects and undertakes a smooth operation of laryngeal surgery.

The above-mentioned specific implementations are intended to be exemplary not to be limiting. In the inspiration of the present invention, those ordinary skills in the art can also make many modifications without breaking away from the subject of the present invention and the protection scope of the claims. All these modifications belong to the protection of the present invention.

What is claimed is:

1. A multispectral switch fiber optic lighting laryngoscope comprising: a laryngoscope handle (110), said laryngoscope handle (110) is configured with a connection part (120), said connection part (120) mechanically connects and fastens a laryngoscope blade (100);

wherein an LED light module (160) is configured in said laryngoscope handle (110), and said LED light module (160) comprises a multispectral LED light (140), said multispectral LED light (140) emits at least two different colors of light from a single light bulb as a light source;

wherein a PCB module (200) is configured in said laryngoscope handle (110), and said PCB module (200) comprises a control circuit (171) and a switch button (180);

wherein said control circuit (171) is electrically connected with said switch button (180) and said multispectral LED light (140) respectively, enabling a user to switch the color of emitted light from the single light bulb and adjust radiation brightness from said multispectral LED light (140) through pressing said switch button (180).

2. The multispectral switch fiber optic lighting laryngoscope according to claim 1, wherein said LED light module (160) further comprises an auxiliary PCB board (150), said multispectral LED light (140) is set up on and electrically connected with said auxiliary PCB board (150); and said LED light module (160) further comprises a light guiding tube (130), said light guiding tube (130) is configured surrounding said multispectral LED light (140).

3. The multispectral switch fiber optic lighting laryngoscope according to claim 2, wherein said PCB module (200) further comprises a main PCB board (170) and a battery (190), said switch button (180) is set up on and electrically connected with said main PCB board (170); said battery (190) is electrically connected with said main PCB board (170);

wherein said main PCB board (170) and said auxiliary PCB board (150) are electrically connected.

4. The multispectral switch fiber optic lighting laryngoscope according to claim 3, wherein said auxiliary PCB board (150) and main PCB board (170) are made of metal substrate materials; said connection part (120) is a general connection hinge.

5. The multispectral switch fiber optic lighting laryngoscope according to claim 1, wherein a fiber optic tube (90) is configured in said laryngoscope blade (100), and an optical fiber is configured in said fiber optic tube (90).

6. The multispectral switch fiber optic lighting laryngoscope according to claim 5, wherein when said connection part (120) mechanically connects and fastens a laryngoscope blade (100), said fiber optic tube (90) and a light guiding tube (130) are physically and optically connected, enabling the light emitted from said multispectral LED light (140) to pass through said light guiding tube (130) and the optical fiber in said fiber optic tube (90) towards a light emitting tip (210) of said laryngoscope blade (100).

7. The multispectral switch fiber optic lighting laryngoscope according to claim 6, wherein said light guiding tube (130) comprises a wide light guiding section (131) and a narrow light guiding section (132), a semicircular tube (133) is configured between said wide light guiding section (131) and said narrow light guiding section (132) for smooth transition of light, maximizing the accumulation and transfer of light emitted from said multispectral LED light (140); and wherein said light guiding tube (130) is made of polycarbonate or polymethyl methacrylate materials.

8. The multispectral switch fiber optic lighting laryngoscope according to claim 1, wherein said control circuit (171) comprises a boosted circuit (173) and a main control chip (172), said boosted circuit (173) is electrically connected with a battery (190) and said main control chip (172) respectively; said switch button (180) is electrically connected with said main control chip (172).

9. The multispectral switch fiber optic lighting laryngoscope according to claim 1, wherein said control circuit (171) further comprises a main control chip (172), a first radiation brightness adjustment circuit (176) and a second radiation brightness adjustment circuit (178), and said first radiation brightness adjustment circuit (176) is electrically connected with said main control chip (172) through a first circuit (1751) and a second circuit (1752) respectively, said first radiation brightness adjustment circuit (176) is electrically connected with said multispectral LED light (140);

said second radiation brightness adjustment circuit (178) is electrically connected with said main control chip (172) through a third circuit (1771) and a fourth circuit (1772) respectively, said second radiation brightness adjustment circuit (178) is electrically connected with said multispectral LED light (140).

\* \* \* \* \*